(12) United States Patent
Soon-Shiong

(10) Patent No.: US 12,350,316 B2
(45) Date of Patent: Jul. 8, 2025

(54) IL7-IL 15 TxM COMPOSITIONS AND METHODS

(71) Applicant: NantBio, Inc., Culver City, CA (US)

(72) Inventor: Patrick Soon-Shiong, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 1180 days.

(21) Appl. No.: 17/263,775

(22) PCT Filed: Aug. 15, 2019

(86) PCT No.: PCT/US2019/046648
§ 371 (c)(1),
(2) Date: Jan. 27, 2021

(87) PCT Pub. No.: WO2020/037120
PCT Pub. Date: Feb. 20, 2020

(65) Prior Publication Data
US 2021/0290729 A1 Sep. 23, 2021

Related U.S. Application Data

(60) Provisional application No. 62/764,875, filed on Aug. 16, 2018.

(51) Int. Cl.
*A61K 38/20* (2006.01)
*A61K 40/11* (2025.01)
*A61K 40/42* (2025.01)
*C12N 5/0783* (2010.01)

(52) U.S. Cl.
CPC .......... *A61K 38/20* (2013.01); *A61K 38/2046* (2013.01); *A61K 40/11* (2025.01); *A61K 40/428* (2025.01); *C12N 5/0636* (2013.01); *C12N 2501/2307* (2013.01); *C12N 2501/2315* (2013.01); *C12N 2501/2321* (2013.01)

(58) Field of Classification Search
CPC ................ A61K 38/20; A61K 38/2046; A61K 38/2086; C12N 5/0636; C12N 2501/2307; C12N 2501/2315; C12N 2501/2321
See application file for complete search history.

(56) References Cited

U.S. PATENT DOCUMENTS

| | | | |
|---|---|---|---|
| 8,507,222 | B2 | 8/2013 | Wong et al. |
| 2006/0165652 | A1 | 7/2006 | Dudley et al. |
| 2016/0355567 | A1 | 12/2016 | Wong et al. |
| 2017/0107285 | A1 | 4/2017 | Jensen |
| 2019/0300591 | A1 * | 10/2019 | Wong ..................... C12N 15/81 |

FOREIGN PATENT DOCUMENTS

| | | |
|---|---|---|
| WO | 96/32478 A1 | 10/1996 |
| WO | 97/34631 A1 | 9/1997 |
| WO | 2017/205726 A1 | 11/2017 |
| WO | WO-2017194924 A1 * | 11/2017 |
| WO | 2020/037120 A1 | 2/2020 |

OTHER PUBLICATIONS

Song et al. In Vivo Antitumor Activity of a Recombinant IL7/IL15 Hybrid Cytokine in Mice. Mol Cancer Ther. Oct. 2016;15(10):2413-2421 (Year: 2016).*
Bowie et al. Deciphering the Message in Protein Sequences: Tolerance to Amino Acid Substitutions. Science, 1990, 247:1306-1310 (Year: 1990).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).*
Whisstock et al. Prediction of protein function from protein sequence and structure. Quarterly Reviews in Biophysics. 36(3):307-340, 2007 (Year: 2007).*
Song et al. Mol Cancer Ther. Oct. 2016;15(10):2413-2421 (Year: 2016).*
Restifo et al., "Big bang theory of stem-like T cells confirmed", Blood, 2014, vol. 124, No. 4, pp. 476-477 (Cited from Specification).
Gattinoni et al., "Removal of homeostatic cytokine sinks by lymphodepletion enhances the efficacy of adoptively transferred tumor-specific CD8+T cells", The Journal of Experimental Medicine, 2005, vol. 202, No. 7, pp. 907-912 (Cited from Specification).
Cieri et al., "IL-7 and IL-15 instruct the generation of human memory stem T cells from naive precursors", 2013, Blood, vol. 121, No. 4, pp. 573-584 (Cited from Specification).
Sabatino et al., "Generation of clinical-grade CD19-specific CAR-modified CD8+ memory stem cells for the treatment of human B-cell malignancies", Blood, 2016, vol. 128, No. 4, pp. 519-528 (Cited from Specification).
Zhu et al., "Novel Human Interleukin-15 Agonists", The Journal of Immunology, 2009, vol. 183, No. 6, pp. 3598-3607 (Cited from Specification).

(Continued)

*Primary Examiner* — Vanessa L. Ford
*Assistant Examiner* — Sandra Carter
(74) *Attorney, Agent, or Firm* — Umberg Zipser LLP; Martin Fessenmaier; Priti Phukan

(57) ABSTRACT

Contemplated compositions and methods are directed to in vivo stimulation of $T_N$ cells to differentiate to $T_{SCM}$ cells in the presence of tumor cells expressing tumor associated antigens or tumor and patient specific neoepitopes using a pharmaceutical composition that includes an IL-15 portion and an IL-7 portion. The $T_{SCM}$ cells are then isolated and expanded in vitro, preferably using a pharmaceutical composition that includes an IL-15 portion, an IL-7 portion, and an IL21 portion, and subsequently administered to the patient.

7 Claims, 7 Drawing Sheets

Specification includes a Sequence Listing.

(56) References Cited

OTHER PUBLICATIONS

Chirifu et al., "Crystal structure of the IL-15-IL-15Rα complex, a cytokine-receptor unit presented in trans", Nature Immunology, 2007, vol. 8, No. 9, pp. 1001-1007 (Cited from Specification).

Han et al.,"IL-15:IL-15 receptor alpha superagonist complex: High-level co-expression in recombinant mammalian cells, purification and characterization", Cytokine, 2011, vol. 56, No. 3, pp. 804-810 (Cited from Specification).

Whitlow et al., "Single-chain Fv proteins and their fusion proteins" Methods, 1991, vol. 2, No. 2, pp. 97-105 (Cited from Specification).

International Search Report and Written Opinion received for PCT Application Serial No. PCT/US2019/046648 dated Dec. 12, 2019, 14 pages.

Kondo et al., "Generation and application of human induced-stem cell memory T cells for 5, 7, 8 adoptive immunotherapy", Cancer Science, Jul. 3, 2018, vol. 109, No. 7, pp. 2130-2140.

International Preliminary Report on Patentability received for PCT Application Serial No. PCT/US2019/046648 dated Feb. 25, 2021, 14 pages.

Morrot Alexandre, "Human stem memory T cells (TSCM) as critical players in the long term persistence of immune responses", Annals of Translational Medicine, 2017, vol. 5, No. 5, pp. 1-2.

Gattinoni et al., "Moving T memory stem cells to the clinic", Immunobiology, 2013, vol. 121, No. 4, pp. 567-568.

Zeng et al., "Synergy of IL-21 and IL-15 in regulating CD8+ T cell expansion and function" The Journal of Experimental Medicine, 2005, vol. 201, No. 1, pp. 139-148.

* cited by examiner

SEQUENCE LISTING

```
<160> NUMBER OF SEQ ID NOS: 2

<210> SEQ ID NO 1
<211> LENGTH: 285
<212> TYPE: PRT
<213> ORGANISM: Artificial Sequence
<220> FEATURE:
<223> OTHER INFORMATION: TxM Construct (IL-7)
<220> FEATURE:
<221> NAME/KEY: MISC_FEATURE
<222> LOCATION: (1)..(18)
<223> OTHER INFORMATION: Leader peptide
<220> FEATURE:
<221> NAME/KEY: MISC_FEATURE
<222> LOCATION: (19)..(171)
<223> OTHER INFORMATION: IL-7
<220> FEATURE:
<221> NAME/KEY: MISC_FEATURE
<222> LOCATION: (172)..(285)
<223> OTHER INFORMATION: IL-15 (N72D)

<400> SEQUENCE: 1

Met Lys Trp Val Thr Phe Ile Ser Leu Leu Phe Leu Phe Ser Ser Ala
1               5                   10                  15

Tyr Ser Asp Cys Asp Ile Glu Gly Lys Asp Gly Lys Gln Tyr Glu Ser
            20                  25                  30
```

```
Val Leu Met Val Ser Ile Asp Gln Leu Leu Asp Ser Met Lys Glu Ile
         35                  40                  45

Gly Ser Asn Cys Leu Asn Asn Glu Phe Asn Phe Phe Lys Arg His Ile
 50                  55                  60

Cys Asp Ala Asn Lys Glu Gly Met Phe Leu Phe Arg Ala Ala Arg Lys
 65                  70                  75                  80

Leu Arg Gln Phe Leu Lys Met Asn Ser Thr Gly Asp Phe Asp Leu Glu
                 85                  90                  95

Ile Leu Leu Lys Val Ser Glu Gly Thr Thr Ile Leu Leu Asn Cys Thr
                100                 105                 110

Gly Gln Val Lys Gly Arg Lys Pro Ala Ala Leu Gly Glu Ala Gln Pro
                115                 120                 125

Thr Lys Ser Leu Glu Glu Asn Lys Ser Leu Lys Glu Gln Lys Lys Leu
                130                 135                 140

Asn Asp Leu Cys Phe Leu Lys Arg Leu Leu Gln Glu Ile Lys Thr Cys
145                 150                 155                 160

Trp Asn Lys Ile Leu Met Gly Thr Lys Glu His Asn Trp Val Asn Val
                165                 170                 175

Ile Ser Asp Leu Lys Lys Ile Glu Asp Leu Ile Gln Ser Met His Ile
                180                 185                 190

Asp Ala Thr Leu Tyr Thr Glu Ser Asp Val His Pro Ser Cys Lys Val
                195                 200                 205

Thr Ala Met Lys Cys Phe Leu Leu Glu Leu Gln Val Ile Ser Leu Glu
                210                 215                 220

Ser Gly Asp Ala Ser Ile His Asp Thr Val Glu Asn Leu Ile Ile Leu
225                 230                 235                 240

Ala Asn Asp Ser Leu Ser Ser Asn Gly Asn Val Thr Glu Ser Gly Cys
                245                 250                 255

Lys Glu Cys Glu Glu Leu Glu Glu Lys Asn Ile Lys Glu Phe Leu Gln
                260                 265                 270

Ser Phe Val His Ile Val Gln Met Phe Ile Asn Thr Ser
                275                 280                 285

<210> SEQ ID NO 2
<211> LENGTH: 448
<212> TYPE: PRT
<213> ORGANISM: Artificial Sequence
<220> FEATURE:
<223> OTHER INFORMATION: TxM Construct (Il-21)
<220> FEATURE:
<221> NAME/KEY: MISC_FEATURE
<222> LOCATION: (1)..(18)
<223> OTHER INFORMATION: Leader peptide
<220> FEATURE:
<221> NAME/KEY: MISC_FEATURE
<222> LOCATION: (19)..(151)
<223> OTHER INFORMATION: IL-21
<220> FEATURE:
<221> NAME/KEY: MISC_FEATURE
<222> LOCATION: (152)..(216)
<223> OTHER INFORMATION: IL-15 Receptor Sushi Domain
<220> FEATURE:
<221> NAME/KEY: MISC_FEATURE
<222> LOCATION: (217)..(448)
<223> OTHER INFORMATION: Human IgG Fc portion

<400> SEQUENCE: 2

Met Lys Trp Val Thr Phe Ile Ser Leu Leu Phe Leu Phe Ser Ser Ala
 1               5                  10                  15

Tyr Ser Gln Gly Gln Asp Arg His Met Ile Arg Met Arg Gln Leu Ile
```

```
            20                  25                  30
Asp Ile Val Asp Gln Leu Lys Asn Tyr Val Asn Asp Leu Val Pro Glu
                35                  40                  45

Phe Leu Pro Ala Pro Glu Asp Val Glu Thr Asn Cys Glu Trp Ser Ala
 50                  55                  60

Phe Ser Cys Phe Gln Lys Ala Gln Leu Lys Ser Ala Asn Thr Gly Asn
 65                  70                  75                  80

Asn Glu Arg Ile Ile Asn Val Ser Ile Lys Lys Leu Lys Arg Lys Pro
                85                  90                  95

Pro Ser Thr Asn Ala Gly Arg Arg Gln Lys His Arg Leu Thr Cys Pro
                100                 105                 110

Ser Cys Asp Ser Tyr Glu Lys Lys Pro Pro Lys Glu Phe Leu Glu Arg
                115                 120                 125

Phe Lys Ser Leu Leu Gln Lys Met Ile His Gln His Leu Ser Ser Arg
                130                 135                 140

Thr His Gly Ser Glu Asp Ser Ile Thr Cys Pro Pro Met Ser Val
145                 150                 155                 160

Glu His Ala Asp Ile Trp Val Lys Ser Tyr Ser Leu Tyr Ser Arg Glu
                165                 170                 175

Arg Tyr Ile Cys Asn Ser Gly Phe Lys Arg Lys Ala Gly Thr Ser Ser
                180                 185                 190

Leu Thr Glu Cys Val Leu Asn Lys Ala Thr Asn Val Ala His Trp Thr
                195                 200                 205

Thr Pro Ser Leu Lys Cys Ile Arg Glu Pro Lys Ser Cys Asp Lys Thr
                210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420             425                 430

Leu His Asn His Tyr Thr Gln Lys Ser Leu Ser Leu Ser Pro Gly Lys
        435                 440             445
```

IL7-IL 15 TxM COMPOSITIONS AND METHODS

This application claims priority to our U.S. provisional patent application with the Ser. No. 62/764,875, which was filed Aug. 16, 2018.

PARTIES TO A JOINT RESEARCH AGREEMENT

Some of the subject matter in this application was made by or on behalf of NantBio Inc and Altor Bioscience LLC as a result of activities undertaken within the scope of a joint research agreement effective on or before the date the claimed invention was made.

SEQUENCE LISTING

The content of the ASCII text file of the sequence listing named 102719.0014PCT_ST25, which is 8 kb in size and which was created on Aug. 5, 2019 and electronically submitted via EFS-Web along with the present application is incorporated by reference in its entirety.

FIELD OF THE INVENTION

The field of the invention is immune therapy of cancer, particularly as it relates to use of memory T cells and especially stem cell memory T cells ($T_{SCM}$) cells.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference, except that where a definition or use of a term in an incorporated reference is inconsistent or contrary to the definition of that term provided herein, the definition of that term provided herein applies and the definition of that term in the reference does not apply.

Persistent adaptive immune response to various antigens, including tumor associated antigens and neoantigens requires cell populations that can support such antigen-specific immune response. For T lymphocytes, long-lasting immune protection is typically achieved by stimulation of differentiation of naïve T cells with an antigen to form central memory T cells ($T_{CM}$) and effector memory T cells ($T_{EFF}$). More recently, memory stem T cells ($T_{SCM}$) have been discovered having high persistence in the host, even in the absence of the specific antigen that triggered their formation. Notably, human $T_{SCM}$ were shown to be multipotent in providing a potential reservoir for T cell memory throughout life, which is highly desirable in the context of tumor antigens.

The therapeutic potential of $T_{SCM}$ was shown in a study where human patients that had received an allogeneic hematopoietic stem cell transplant (HSCT) together with relatively low doses of streptamer-enriched human CMV-specific CD8$^+$ T cells produced a robust pathogen-specific T-cell expansion. Notably, antiviral T cells, including CD62L$^+$ $T_{SCM}$ cells were capable of massive proliferation and at least potential indefinite persistence (see e.g., Blood 2014 124:476-477). Unfortunately, $T_{SCM}$ are relatively rare. While it is known that T cell proliferation for certain T cells can be stimulated in vitro with various cytokines, the cytokine quantities required are often undesirably high for in vivo use and may still not provide sufficient numbers of $T_{SCM}$ cells (see e.g., J Exp Med 2005; 202 (7): 907-912).

More recently, it was reported that $T_{SCM}$ were generated from precursors using IL7 and IL15 (see e.g., Blood 2013 121:573-584). Interestingly, CD19-CAR modified $T_{SCM}$ could also be produced by incubation of specific T cell precursor cells with IL7 and IL21 (see e.g., Blood 2016 128:519-528). However, while at least conceptually promising, the stimulation of T cells required high quantities of cytokines that, if administered in vivo, would likely trigger adverse events and would also lack persistence in blood.

Even though there are numerous therapeutic agents known in the art, all or almost all of them suffer from various disadvantages. Therefore, there remains a need for improved immunotherapeutic compositions, especially as it relates to cancer immune therapy using cancer specific $T_{SCM}$ cells.

SUMMARY OF THE INVENTION

The inventors have now discovered systems and methods by which a large quantity of tumor specific $T_{SCM}$ cells can be prepared in a conceptually simple and effective manner. In preferred aspects, differentiation of naïve $T_N$ cells to $T_{SCM}$ cells is performed in a patient with a tumor using specific cytokine stimulation to so obtain $T_{SCM}$ cells with T cell receptor specificity against the tumor. These $T_{SCM}$ cells are then isolated from the patient and ex vivo expanded using a further specific cytokine set to so produce large quantities of $T_{SCM}$ cells suitable for therapy. Advantageously, expansion is performed under conditions that avoid differentiation of the isolated cells into $T_{EFF}$ cells.

In one aspect of the inventive subject matter, the inventors contemplate a method of generating a therapeutic cell composition for treatment of cancer that includes a step of administering to an individual a chimeric molecule complex comprising an IL-15 portion and optionally an IL-7 portion to stimulate in the individual differentiation of $T_N$ cells to $T_{SCM}$ cells. Most typically, the individual has a tumor with tumor cells that express a tumor associated antigen or a tumor and patient specific neoepitope, and administration of the chimeric molecule complex is performed while the tumor cells are in the individual. As such, the tumor can advantageously be used as an antigenic source for the $T_{SCM}$ cells. The $T_{SCM}$ cells are then isolated from the individual and in vitro expanded.

Therefore, and viewed from a different perspective, the inventors also contemplate a method of treating an individual with a therapeutic cell composition that includes a step of administering to an individual a chimeric molecule complex comprising an IL15 portion and optionally an IL7 portion to stimulate differentiation of $T_N$ cells to $T_{SCM}$ cells. Most typically, the individual has a tumor with tumor cells that express a tumor associated antigen or a tumor and patient specific neoepitope, and the step of administering is performed when the tumor cells are in the individual. Such methods will also include a step of isolating the $T_{SCM}$ cells from the individual, a step of in vitro expanding the isolated $T_{SCM}$ cells, and a step of infusing the expanded $T_{SCM}$ cells to the individual. Where desired, the step of infusing the expanded $T_{SCM}$ cells to the individual may be performed in conjunction with a cancer vaccine (e.g., after administration of the cancer vaccine).

Preferably, but not necessarily, contemplated methods may include a further step of lymphodepletion before the step of administering the chimeric molecule complex, and/or the chimeric molecule complex is an IL-7 TxM or ALT-803. It is also contemplated that the $T_{SCM}$ cells are isolated from the individual using CD62L or CCR7, for example, using a FACS process or leukapheresis.

It is further contemplated that such methods may include a step of selecting from the isolated $T_{SCM}$ cells a sub-population of cells that have a T cell receptor that binds the tumor associated antigen or the tumor and patient specific neoepitope, and/or that the step of in vitro expanding the isolated $T_{SCM}$ cells is performed using a chimeric molecule complex comprising an IL15 portion, an IL7 portion, and an IL-21 portion. Moreover, it is contemplated that the step of in vitro expanding the isolated $T_{SCM}$ cells is performed in the presence of the tumor associated antigen or the tumor and patient specific neoepitope, and/or in the presence of dendritic cells (which may be exposed to or express the tumor associated antigen or the tumor and patient specific neoepitope) of the individual.

Consequently, the inventors also contemplate a method of treating an individual with a therapeutic cell composition that includes a step of in vivo stimulating $T_N$ cells in the individual to differentiate to $T_{SCM}$ cells, wherein the step of stimulating is performed in the presence of tumor cells that express a tumor associated antigen or a tumor and patient specific neoepitope. Such methods will further include a step of isolating the $T_{SCM}$ cells from the individual, and in vitro expanding the isolated $T_{SCM}$ cells, and a further step of administering the expanded $T_{SCM}$ cells to the individual.

Most typically, the step of in vivo stimulating the $T_N$ cells is performed after a prior step of lymphodepletion, and/or the step of in vivo stimulating the $T_N$ cells is performed using a pharmaceutical composition comprising an IL-15 portion and/or an IL-7 portion. It is further generally contemplated that the $T_{SCM}$ cells are isolated using whole leukapheresis or FACS sorting. Where desired, the step of isolating the $T_{SCM}$ cells may also include a further step of isolating a sub-population of $T_{SCM}$ cells that have a T cell receptor that binds the tumor associated antigen or the tumor and patient specific neoepitope.

As noted before, it is generally contemplated that the step of in vitro expanding the isolated $T_{SCM}$ cells is performed using a pharmaceutical composition comprising an IL-15 portion, an IL-7 portion, and/or an IL-21 portion (e.g., using a TxM comprising an IL-15 portion, an IL-7 portion, and an IL-21 portion). In further aspects of contemplated methods, the step of in vitro expanding the isolated $T_{SCM}$ cells may be performed in the presence of the tumor associated antigen or the tumor and patient specific neoepitope, and/or in the presence of dendritic cells (which may be exposed to or express the tumor associated antigen or the tumor and patient specific neoepitope) of the individual.

Therefore, the inventors also contemplate a pharmaceutical composition comprising an IL-15 portion and an IL-7 portion for use in stimulating $T_N$ cells in an individual to differentiate to $T_{SCM}$ cells after lymphodepletion, wherein the individual has tumor cells that express a tumor associated antigen or a tumor and patient specific neoepitope. For example, the IL-15 portion and the IL-7 portion may be part of a TxM molecule. In further aspects, the use may further include a step of isolating the $T_{SCM}$ cells, and/or a step of in vitro expanding the isolated $T_{SCM}$ cells.

Various objects, features, aspects and advantages of the inventive subject matter will become more apparent from the following detailed description of preferred embodiments, along with the accompanying drawing.

DETAILED DESCRIPTION

Figure 1:
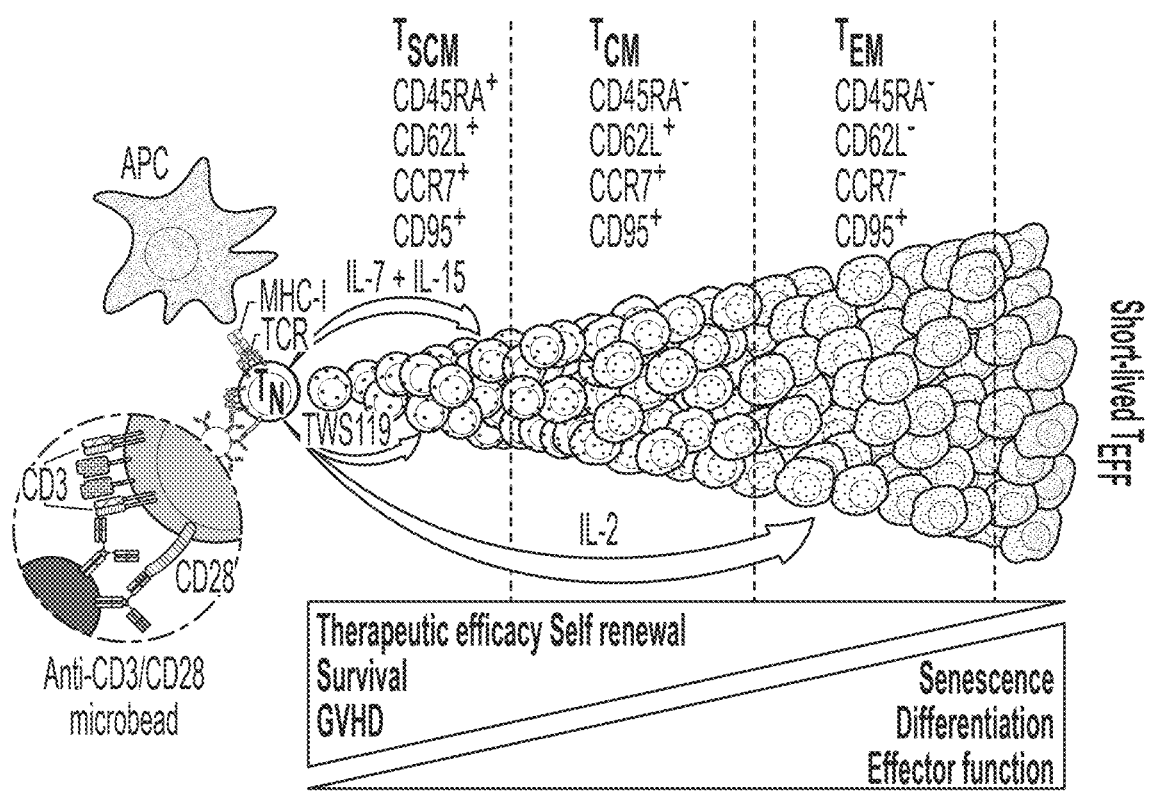
FIG. 1 is a schematic illustration of various memory T cells and selected associated markers and characteristics.

The inventors have now discovered that tumor specific $T_{SCM}$ cells can be prepared in sufficient quantities for immune therapy in a process that uses in vivo stimulation to trigger differentiation of naïve $T_N$ cells to $T_{SCM}$ using tumor cell epitopes as relevant antigens and ex vivo expansion of $T_{SCM}$ cells. Advantageously, expansion is performed under conditions that avoid differentiation of the isolated cells into $T_{EFF}$ cells. In most preferred aspects, IL-7/IL-15 signaling or IL-15 signaling is used in vivo to superselect early memory stem cells, with IL15 inducing their proliferation while IL-7/IL-15/IL-21 signaling is used to expand the $T_{SCM}$ cells without triggering $T_{EFF}$ cell formation.

For example, in one especially preferred aspect of the inventive subject matter, ALT-803 or an IL-7/IL-15 TxM are used to stimulate in a patient having a tumor the differentiation and in vivo growth of stem cell memory CD8 $T_{SCM}$ cells, effector memory $T_{EM}$ cells, and central memory CD8 $T_{CM}$ cells. These cells and especially $T_{SCM}$ cells are then harvested from blood (e.g., by leukophoresis or FACS), typically using markers such as CD62L, CCR7, and/or CD45RA. If desired, the so harvested cells may be further selected for those cells that express a T cell receptor (TCR) that binds to a tumor associated antigen or patient and tumor specific neoepitope. The isolated cells are then grown in vitro with IL-7, IL-15, and IL-21 (e.g., in the form of a IL-7/IL-15/IL-21 TxM) in the presence or absence of tumor related antigens, which may be presented on dendritic or other antigen presenting cells. Upon generation of sufficient numbers of $T_{SCM}$ cells, the $T_{SCM}$ cells are re-infused to the patient to enhance tumor clearance. Similarly, $T_{SCM}$ cells from the patient could also be grown ex vivo as described above and then transfected with a nucleic acid that encodes a suitable TCR (e.g., from single cell sequencing or T cells exposed to known antigens presented on APCs) that binds to the a tumor associated antigen or patient and tumor specific neoepitope.

In still further contemplated aspects, to increase $T_{SCM}$ recovery from the patient even more, the patient may be subjected to an at least partial lymphodepletion prior to the administration of the ALT-803 or an IL-7/IL-15 TxM (or administration of L-7 and IL-15) using modalities well known in the art, such cyclophosphamide (cytoxan) and fludarabine (Fludara), and/or radiation. Advantageously, lymphodepletion will not only depress the numbers of regulatory T cells (Tregs) and myeloid-derived suppressor cells (MDSC), and as such reduce an immune suppressive environment, but will also stimulate endogenous processes that favor formation of $T_{SCM}$ cells. Notably, as the patient tumor cells provide various tumor associated antigens and/or patient and tumor specific antigens, the population of $T_{SCM}$ cells that have a TCR that binds to the a tumor associated antigen or patient and tumor specific neoepitope is significantly increased. Moreover, to even further stimulate such tumor specific $T_{SCM}$ cell population, the ALT-803 or an IL-7/IL-15 TxM can be modified to include a binding portion that is specific to the tumor associated antigen or patient and tumor specific neoepitope.

Therefore, it should be appreciated that relatively large quantities of $T_{SCM}$ cells can be obtained from a patient where the tumor cells in the patient serves as an antigen sink and as such assists in generation of a larger fraction of tumor specific $T_{SCM}$ cells. In addition, at least partial lymphodepletion can be added to a protocol to even further increase the number of (tumor specific) $T_{SCM}$ cells. As will be readily appreciated, $T_{SCM}$ cells can be isolated from whole blood using a variety of processes, including leukapheresis and FACs sorting. Most typically, such separation will employ markers of $T_{SCM}$ cells such as CD62L, CCR7, and/or CD45RA.

In vitro expansion of the isolated $T_{SCM}$ cells can then be performed using cell culture conditions well known in the art. However, the culture medium will also be supplemented with IL7, IL-15, and IL-21 (or chimeric molecules comprising one or more of IL7, IL-15, and IL-21). Most preferably, but not necessarily, the IL7, IL-15, and IL-21 portions will be in a single chimeric molecule complex, a IL-7/IL-15/IL-21 TxM as is described in more detail below. It should be particularly appreciated that IL-17 will stimulate $T_{SCM}$ cell development while IL-15 will stimulate proliferation of such cells. Most advantageously, IL-21 will reduce or even prevent further differentiation of $T_{SCM}$ cells towards $T_{EFF}$ cells such as Tregs and MDSCs. A developmental schematic of stimulated $T_N$ cells is shown in FIG. 1. As can be seen from FIG. 1, therapeutic efficacy decreases with increasing linear differentiation. Thus, use of IL-21 to prevent differentiation to $T_{EFF}$ advantageously increases the fraction of expanded $T_{SCM}$ cell populations. Upon reaching cell numbers sufficient for transfusion (e.g., at least $10^6$, or at least $10^7$, or at least $10^8$, or at least $10^9$ $T_{SCM}$ cells), the cells are then harvested and formulated for transfusion into the patient, preferably in conjunction with other immune therapeutic treatments such as a cancer vaccine, administration of NK cells, and/or checkpoint inhibitors.

In general, it should be noted that the cytokines used herein can be administered as individual isolated and purified cytokines. For example, the cytokines may be administered to the patient individually as IL-7 and IL-15 in any route and dosage commonly given. In the same ways, cytokines may be used in the in vitro expansion individually as IL-7, IL-15, and IL-21. However, it is generally preferred that the cytokines will be administered as part of a chimeric molecule or chimeric molecule complex, and most preferably as an ALT-803 and/or a TxM as is shown in more detail below. Such TxM molecules may include one or more cytokine portions, and most preferably a IL-15/IL-15 receptor alpha portion as is also shown in more detail below. Furthermore, it is contemplated that the TxM constructs or ALT-803 may also include a binding portion (preferably a scFv portion) that binds to a TAA (tumor associated antigen) or neoepitope on the tumor cell to so exhibit specific activity at the tumor cell.

Regardless of the particular arrangement, it should be appreciated that the so formed chimeric molecule complexes will allow for a combination of specific biological effects that provide activity in an enhanced manner over a prolonged period of time. Moreover, where the chimeric complexes include an affinity portion (e.g., scFv), such effects can be further targeted to specific locations. For example, the affinity portions may target tissue (and especially tumor) specific markers to so direct and maintain the effects at a desired location. Among other biological effects, particularly preferred biological effects are those that trigger development and/or proliferation of various memory T cells and especially $T_{SCM}$ cells as is shown in more detail below. In addition, it should be appreciated that the differentiation and proliferation of naïve T cells to various T memory cells can be further enhanced by ligands to TNF superfamily receptors, and especially single and multimeric forms of 4-1BBL (which may form higher order multimers) and/or an agonistic mAb against 4-1BB. Advantageously, IL15 activates T cells and promotes expression of 4-1BB, whereas IL7 and IL21 promote differentiation of T cells to selected memory T cells, and particularly $T_{SCM}$. In the presence of 4-1BBL or agonistic mAb against 4-1BB, proliferation of such memory T cells is further stimulated.

Furthermore, it should be recognized that contemplated chimeric molecule complexes have significantly increased persistence (i.e., extended serum half life time), which allows the molecule to perform its functions while delaying degradation in the blood stream. Indeed, it was observed that the Fc portion significantly increased the lifespan of IL15 in circulation as compared to IL15 per se. This provides the chimeric molecule complex with persistence, thus prolonging the activity of the molecule in circulation. Another contemplated benefit, as is discussed in more detail below, is that the Fc portion greatly simplifies purification processes during the preparation of purified chimeric molecule complexes. As already noted above, the Fc portion may include at least an Fc portion of an IgG, IgM, IgA, IgD, or IgE antibody.

It is contemplated that a preferred arrangement of the first fusion protein, from N- to C-terminus, is as follows: first affinity portion, IL15 receptor, Fc portion. However, the first fusion protein may also be arraigned as follows: IL15 receptor, Fc portion, first affinity portion. Ideally, the second affinity portion is arranged, from N- to C-terminus as follows: second affinity portion, IL15 portion.

With respect to the production of contemplated chimeric molecule complexes and dimers/multimers, various methods of synthesis are contemplated. For example, and in general, it is contemplated that chimeric molecule complexes can be expressed from one or more nucleic acid in patient cells in vivo, in patient or mammalian production cells (e.g., CHO cells) in vitro, or where desired in other cells such as bacteria, yeast, or non-mammalian cells. Most preferably, the individual components of the fusion proteins (e.g., IL15 or IL15Rα, Fc portion, affinity portions, etc.) are expressed from a recombinant nucleic acid as a single polypeptide, typically with short and flexible linker sequences in between the individual components. However, in less preferred aspects, the individual components can be expressed individually and are then coupled together after expression. Such coupling will typically include use of high-affinity binding pairs such as biotin/avidin, protein A/G, short nucleic acids with sequence complementarity, etc. Most preferably, the fusion protein (components) of the chimeric molecule complex will be co-expressed within the same cell.

For example, contemplated chimeric molecule complexes can be prepared as an IL7 (or IL18)/huIL15N72D fusion protein in complex with (i.e., non-covalently bound to) an IL21 (or IL12)/huIL15RaSu/huIgG1 Fc fusion protein using sequences known in the art. For example, with respect to IL15 it is contemplated that all known IL15 sequences are deemed suitable for use herein, and particularly human or humanized IL15. Thus, the term "IL15" as used herein refers to all IL15 forms (including isoforms, prepro, and pro forms), preferably mammalian, and most preferably human or humanized forms. Moreover, contemplated IL15 proteins also include mutant forms, and particularly mutants with higher biological activity such as N72D mutant form (see e.g., Zhu et al., *J Immunol*, 183:3598-3607, 2009). For example, suitable IL15 sequences can be found under Genbank accession numbers X91233 (Genomic DNA), CH471056 (Genomic DNA), or X94223 (mRNA), AK290619 (mRNA), BC100961 (mRNA), and the protein sequence is known under UniProtKB identifier P40933.

Similarly, with respect to the IL15 receptor it is contemplated that all known IL15 receptor sequences are deemed suitable for use herein. However, especially preferred receptor sequences are high-affinity IL15R alpha chain (IL15Rα) receptors, and particularly human or humanized IL15Rα. Thus, the term "IL15 receptor" as used herein refers to all IL15R forms (including all isoforms), preferably mammalian, and most preferably human or humanized forms. For example, suitable IL15Rα sequences can be found under Genbank accession number AY316538 (Genomic DNA), CH471072 (Genomic DNA), or CR457064 (mRNA), AK304211 (mRNA), BC121140 mRNA, and the protein sequence is known under UniProtKB identifier Q13261.

As discussed above, the fusion proteins may also comprise an Fc domain of an antibody. Most typically, Fc domains will ultimately be present as a dimer as exemplarily shown in FIG. 2B. Moreover, it is generally preferred that immunoglobulin from which the Fc domain is obtained is a mammalian, and most preferably human immunoglobulin, and especially IgG1 and IgG2. Other suitable Fc domains may be derived from different Ig classes (such as IgG, IgA, IgE) or subclasses (e.g., IgG1, IgG2, IgG3, IgA1, IgGA2) or variants thereof (see e.g., WO 97/34631 and WO 96/32478). Fc domains are well known in the art and suitable sequences can be obtained from publically available sources such as GenBank, EMBL, SwissProt, etc.

In a particularly preferred example, a first fusion protein containing IL15Rα (or portion thereof) comprises a first cytokine portion coupled via a linker to a hu-IL15RαSu portion coupled via a linker to a hu-IgG1 Fc portion. Such first fusion protein forms a complex (via IL15/IL15Rα binding) with a second fusion protein containing IL15 (or portion thereof) that comprises a second cytokine portion coupled via a linker (as discussed below) to a hu-IL15N72D portion. Such complex may then form an antibody-like dimer via interaction and disulfide bond formation of the two Fc portions.

Most typically, the IL-15:IL-15Rα complex is a complex having IL-15 non-covalently bound to the soluble IL-15Rα domain of the native IL-15Rα. In some cases, the soluble IL-15Rα is covalently linked to a biologically active polypeptide and/or to an IgG Fc domain. The IL-15 can be either IL-15 or IL-15 covalently linked to a second biologically active polypeptide. The crystal structure of the IL-15:IL-15Rα complex is known (see e.g., 2007 *Nat Immunol* 8, 1001-1007).

In various embodiments of the above aspects or any other aspect of the invention presented herein, the IL-15Rα fusion protein comprises soluble IL-15Rα, e.g., IL-15Rα covalently linked to a biologically active polypeptide (e.g., the heavy chain constant domain of IgG, an Fc domain of the heavy chain constant domain of IgG, or a cytokine). In other embodiments of the invention of the above aspects, IL-15 comprises IL-15, e.g., IL-15 covalently linked to a second biologically active polypeptide, e.g., a cytokine or a binding portion (e.g., scFv). In other embodiments, purifying the IL-15:IL-15Rα complex from the host cell or media involves capturing the IL-15:IL-15Rα complex on an affinity reagent that specifically binds the IL-15:IL-15Rα fusion protein complex. In other embodiments, the IL-15Rα fusion protein contains an IL-15Rα/Fc fusion protein and the affinity reagent specifically binds the Fc domain. In other embodiments, the affinity reagent is Protein A or Protein G. In other embodiments, the affinity reagent is an antibody. In other embodiments, purifying the IL-15:IL-15Rα complex from the host cell or media comprises ion exchange chromatography. In other embodiments, purifying the IL-15:IL-15Rα complex from the host cell or media comprises size exclusion chromatography.

In other embodiments, the IL-15Rα comprises IL-15Ra-Sushi (IL-15RαSu). In other embodiments, the IL-15 is a variant IL-15 (e.g., IL-15N72D). In other embodiments, the IL-15 binding sites of the IL-15:IL-15Rα complex are fully occupied. In other embodiments, both IL-15 binding sites of the IL-15:IL-15RαSu/Fc complex are fully occupied. In other embodiments, the IL-15:IL-15Rα complex is purified based on the complex charge or size properties. In other embodiments, the fully occupied IL-15N72D:IL-15RαSu/Fc fusion protein complex is purified by anion exchange chromatography based on the complex charge properties. In other embodiments, the fully occupied IL-15N72D:IL-15RαSu/Fc fusion protein complex is purified using a quaternary amine-based resin with binding conditions employing low ionic strength neutral pH buffers and elution conditions employing buffers of increasing ionic strength.

In certain embodiments of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt) and variants thereof are referred to using the native amino acid, its position in the mature sequence and the variant amino acid. For example, huIL15N72D refers to human IL-15 comprising a substitution of N to D at position 72. In certain embodiments, the IL-15 variant functions as an IL-15 agonist as demonstrated, e.g., by increased binding activity for the IL-15RI37C receptors compared to the native IL-15 polypeptide. In certain embodiments, the IL-15 variant functions as an IL-15 antagonist as demonstrated by e.g., decreased binding activity for the IL-15RI3yC receptors compared to the native IL-15 polypeptide. In certain embodiments, the IL-15 variant has increased binding affinity or a decreased binding activity for the IL-15Rf3yC receptors compared to the native IL-15 polypeptide. In certain embodiments, the sequence of the IL-15 variant has at least one (i.e., 1, 2, 3, 4, 5, 6, 7, 8, 9, 10, or more) amino acid change compared to the native IL-15 sequence. The amino acid change can include one or more of an amino acid substitution or deletion in the domain of IL-15 that interacts with IL-15R13 and/or IL-15RyC. In certain embodiments, the amino acid change is one or more amino acid substitutions or deletions at position 8, 61, 65, 72, 92, 101, 108, or 111 of the mature human IL-15 sequence. For example, the amino acid change is the substitution of D to N or A at position 8, D to A at position 61, N to A at position 65, N to R at position 72 or Q to A at position 108 of the mature human IL-15 sequence, or any combination of these substitutions. In certain embodiments, the amino acid change is the substitution of N to D at position 72 of the mature human IL-15 sequence.

Figure 2A:
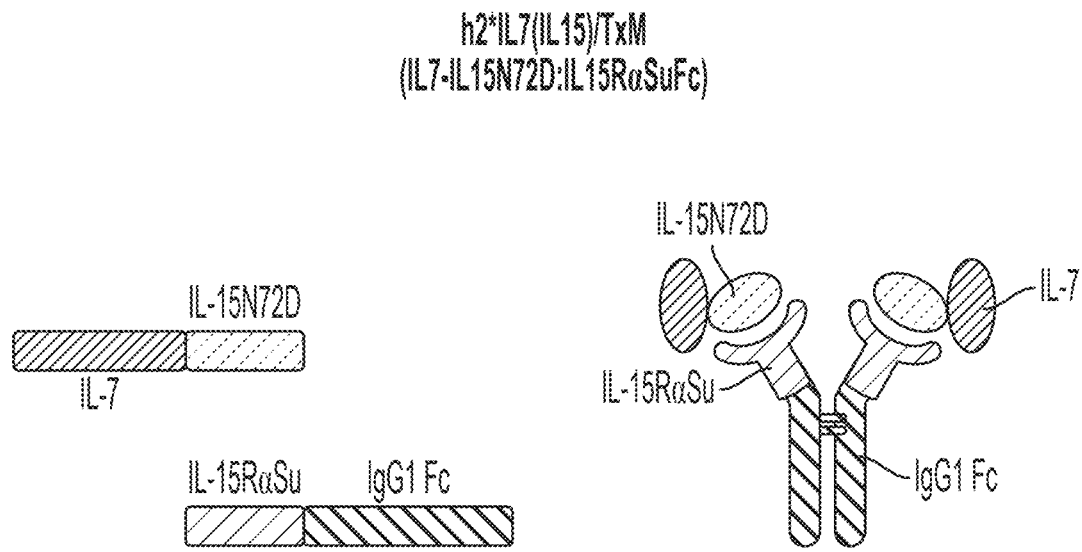
FIG. 2A schematically shows an exemplary chimeric molecule complex comprising an IL-7 portion and an IL-15 portion.
Figure 2B:
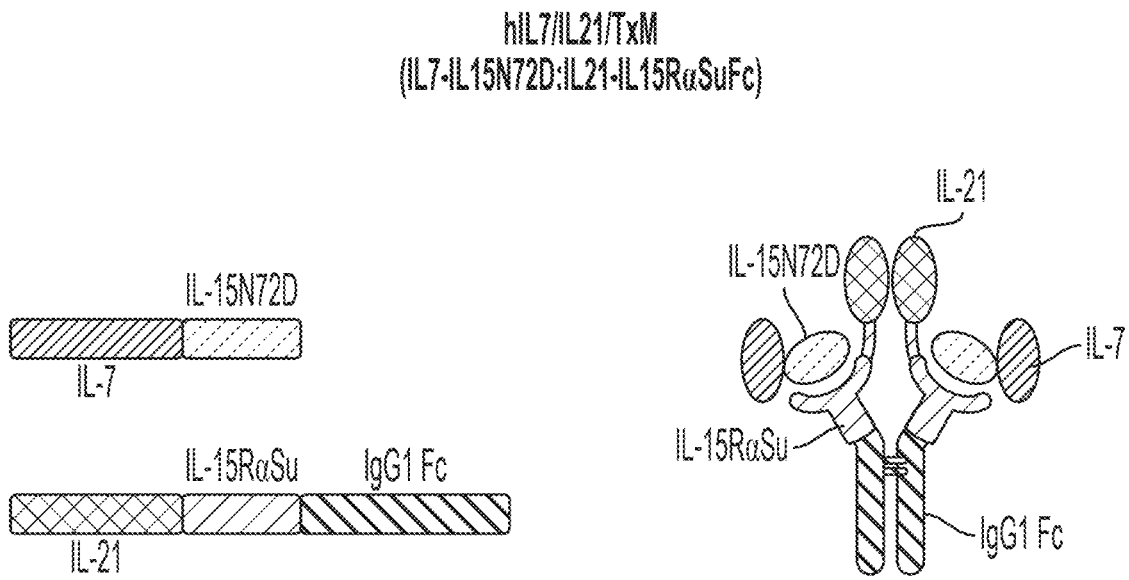
FIG. 2B schematically shows an exemplary chimeric molecule complex comprising a human IL-7 portion, an IL-15 portion, and a human IL-21 portion.
Figure 2C:
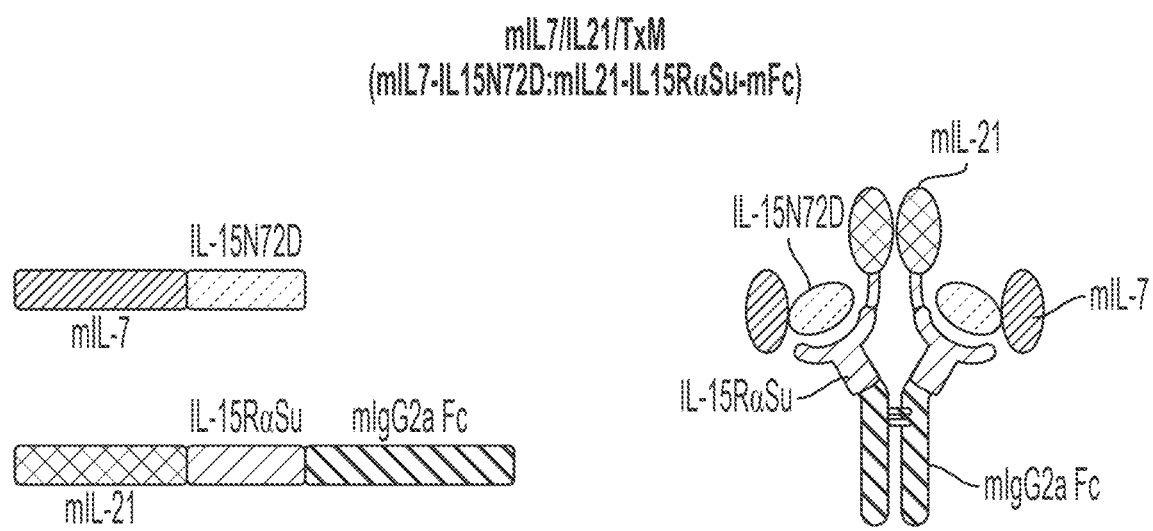
FIG. 2C schematically shows an exemplary chimeric molecule complex comprising a murine IL-7 portion, an IL-15 portion, and a murine IL-21 portion.
Figure 3:
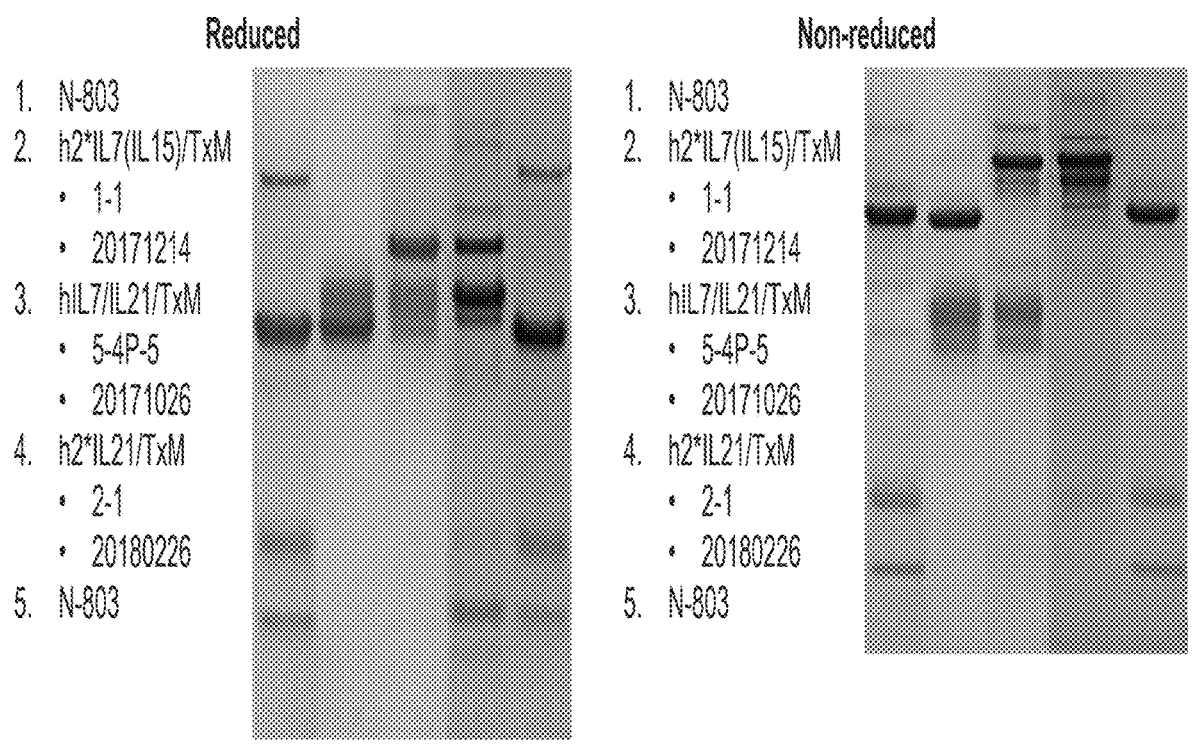
FIG. 3 depicts SDS-PAGE runs of exemplary chimeric molecule complexes with lane content as indicated.

FIG. 2A depicts an exemplary IL-7/IL-15 TxM chimeric molecule complex, while FIG. 2B depicts an exemplary IL-7/IL-15/IL-21 TxM (human) chimeric molecule complex with the domains as indicated and FIG. 2C depicts an exemplary IL-7/IL-15/IL-21 TxM (murine) chimeric molecule complex with the domains as indicated. FIG. 3 illustrates SDS-PAGE runs of selected chimeric molecule complexes under reducing and non-reducing conditions, with lane loading shown to the left of the gel.

In TxM constructs where IL-7 is used, a typical sequence arrangement has a leader peptide (underlined) followed by the IL-7 sequence, which is followed by the IL-15N72D domain (italics).

[SEQ ID NO: 1]
MKWVTFISLLFLFSSAYSDCDIEGKDGKQYESVLMVSIDQLLDSMKEIG

SNCLNNEFNFFKRHICDANKEGMFLFRAARKLRQFLKMNSTGDFDLEIL

LKVSEGTTILLNCTGQVKGRKPAALGEAQPTKSLEENKSLKEQKKLNDL

CFLKRLLQEIKTCWNKILMGTKEH*NWVNVISDLKKIEDLIQSMHIDATL*

*YTESDVHPSCKVTAMKCFLLELQVISLESGDASIHDTVENLIILANDSL*

*SSNGNVTESGCKECEELEEKNIKEFLQSFVHIVQMFINTS*.

In TxM constructs where IL-21 is used, a typical sequence arrangement has a leader peptide (underlined) followed by the IL-21 sequence, which is followed by the IL-15R sushi domain (italics), which in turn is followed by a human IgG1 Fc domain (bold):

[SEQ ID NO: 2]
MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

*SEDSITCPPPMSVEHADIWVKSYSLYSRERYICNSGFKRKAGTSSLTEC*

*VLNKATNVAHWTTPSLKCIR*EPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK.

Notably, contemplated Fc fusion proteins will have an in vivo pharmacokinetic profile comparable to that of human IgG with a similar isotype, and as such substantially increase the halflife time (up to 21 days) as compared to IL15 alone. For example, the pharmacokinetics and biological activity of a IL15 super-agonist (IL15N72D) was dramatically increased by binding the IL15N72D to a IL15Rα/Fc fusion protein (ALT-803), such that the super agonist complex has at least 25-times the activity of the native cytokine in vivo (see e.g., *Cytokine*, 56:804-810, 2011). Such advantage is expected to persist where such or similar scaffolds are used to carry one or more affinity portions.

As noted above, contemplated fusion proteins will preferably include a (preferably flexible) peptide linker between each of the individual components complexes. Most typically, suitable linker sequences will include between about 7 to 20 amino acids, and preferably between about 10 to 20 amino acids. In further preferred aspects, suitable linker sequences are preferably flexible to reduce steric hindrance and/or facilitate proper folding/tertiary structure. Thus, linkers may include amino acids with small side chains, such as glycine, alanine, and serine, to provide for flexibility (G4S linker). Where desired, such mini-sequences may be repeated to achieve a desired length. However, numerous alternative linker sequences are also deemed suitable and appropriate linkers are known in the art (e.g., Whitlow, M. et al., (1991) *Methods: A Companion to Methods in Enzymology*, 2:97-105). Therefore, most typically a linker sequence is between the affinity portion and the IL15 or IL15Rα, and between the IL15Rα and the Fc portion.

Suitable cytokine sequences include all known cytokine sequences, and especially those for IL7, IL12, IL15, IL18, and IL21. Preferably, the cytokine sequences are mammalian cytokines, and especially human cytokine sequences. For example, suitable mammalian and human IL7 protein sequences and isoforms are known from UniProtKB record P13232, and suitable mammalian and human IL12 protein sequences and isoforms for alpha and beta subunits are known from UniProtKB records E7ENE1 and E9PGR3, while suitable mammalian and human IL18 protein sequences and isoforms are known from UniProtKB record Q14116, and suitable mammalian and human IL21 protein sequences and isoforms are known from UniProtKB record Q9HBE4. As will be readily appreciated, all amino acid sequences can be back-translated into corresponding DNA sequences using appropriate codon usage or codon optimization in the respective production cell where the chimeric molecules are recombinantly produced. Moreover, it should be appreciated that all mutant forms are also expressly deemed suitable for use herein, particularly where the mutant protein has increased biological activity as compared with the wildtype form.

Most preferably, contemplated fusion proteins are encoded on a recombinant nucleic acid, typically with codon usage adapted to the host cell that is used to express the fusion proteins. Moreover, it should be appreciated that the chimeric fusion protein complexes may be produced in vivo or in vitro. Therefore, the recombinant nucleic acid may be part of a viral nucleic acid (e.g., recombinant adenovirus that also encodes one or more neoepitopes or polytopes, optionally with co-stimulatory molecules) or part of a DNA vaccine. Alternatively, the recombinant nucleic acid may be a RNA or DNA that is transfected into a production cell to generate recombinant protein. Preferably, the recombinant nucleic acid is part of a vector for extrachromosomal replication such as a phage, virus, plasmid, phagemid, cosmid, or YAC. In particularly preferred aspects, a DNA plasmid is constructed to encode the fusion proteins contemplated herein and is used to prepare the complexes in clinically meaningful quantities. To that end, the recombinant nucleic acid can be inserted into an appropriate expression vector (i.e., a vector that contains the necessary elements for the transcription and translation of the inserted protein-coding sequence). A variety of host-vector systems may be utilized to express the protein-coding sequence, including mammalian cell systems infected with a virus (e.g., vaccinia virus, adenovirus, etc.), insect cell systems infected with virus (e.g., baculovirus), microorganisms such as yeast containing yeast vectors, or bacteria transformed with bacteriophage DNA, plasmid DNA or cosmid DNA. Depending on the host-vector system utilized, any one of a number of suitable transcription and translation elements may be used. The fusion proteins described herein are preferably produced by standard recombinant DNA techniques. Further suitable expression vectors and systems are described is U.S. Pat. No. 8,507,222. As will be readily appreciated, the two components of the chimeric molecule complex can be co-expressed to obtain the suitable chimeric molecule complex.

Another advantage of contemplated compositions and methods is that the step of purification is greatly simplified because the entire chimeric molecule complex can be pulled out of solution by the binding of the Fc portion to a corresponding affinity protein. Therefore, in preferred embodiments, the Fc portion is ideally long enough to (a) facilitate the isolation of the chimeric molecule complex with any affinity protein that binds to the Fc portion (e.g. Protein A or G), and/or (b) facilitate the binding to the Sudlow II domain in albumin. Thus it is contemplated that in at least some embodiments the chimeric molecule complex can be administered as protein complexes with albumin. It is also contemplated that IL15 can be further coupled to alpha-CD3, cellulose binding protein, and/or oligohistidine for the purpose of easier affinity purification. Alternatively, IL15 could be bound to IL2 or another cytokine portion to further enhance activation capability.

When forming dimers, it is contemplated that first and second chimeric molecule complexes can be made in separate batches as homodimers. The batches can then be combined and a reducing agent can then be added to split the bonds between homodimers so the chimeric molecule complexes dissociate. The reducing agent can then be pulled out (e.g. via dialysis), which will cause chimeric molecule complexes to re-associate, but this time in 1st-1st, 2nd-2nd, and 1st-2nd combinations. Further details and methods of producing fusion proteins based on IL15/IL15Rα are described in WO 2017/205726, which is incorporated by reference herein.

It should further be appreciated that the fusion proteins of the inventive subject matter can be combined with any appropriate pharmaceutically acceptable amount in any quantities, and will generally present in an amount of 1-95% by weight of the total weight of the composition. Contemplated compositions may be provided in a dosage form that is suitable for parenteral (e.g., subcutaneous, intravenous, intramuscular, intravesicular, intratumoral or intraperitoneal) administration route. As will be appreciated, pharmaceutical compositions contemplated herein may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). In addition, the formulations may further include appropriate excipients that, upon administration, release the therapeutic agent in a controlled manner. Examples include single or multiple unit tablet or capsule compositions, oil solutions, suspensions, emulsions, microcapsules, microspheres, molecular complexes, nanoparticles, patches, and liposomes.

Most preferably, however, the pharmaceutical compositions comprising a fusion protein complex of the invention may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include one or more co-solvents, e.g. 10-60% w/w of propylene glycol.

Human dosage amounts are initially determined by extrapolating from the amount of compound used in mice or non-human primates, as a skilled artisan recognizes it is routine in the art to modify the dosage for humans compared to animal models. For example, the dosage may vary from between about 1 μg compound/kg body weight to about 50 mg compound/kg body weight; or from about 5 mg/kg body weight to about 40 mg/kg body weight or from about 10 mg/kg body weight to about 30 mg/kg body weight; or from about 50 mg/kg body weight to about 20 mg/kg body weight; or from about 100 mg/kg body weight to about 10 mg/kg body weight; or from about 150 mg/kg body weight to about 500 mg/kg body weight. For example, the dose is about 0.01, 0.05, 0.1, 1, 5, 10, 25, 50, 75, 100, 150, 200,250, 300, 350, 400, 450, 500, 550, 600, 650, 700, 750, 800, 850, 900, 950, or 1,000 mg/kg body weight. Alternatively, doses are in the range of about 5 mg compound/Kg body weight to about 20 mg compound/kg body weight. In another example, the doses are about 0.01, 0.05, 0.1, 1, 5, 8, 10, 12, 14, 16 or 18 mg/kg body weight.

It is contemplated that in preferred embodiments, chimeric molecule complexes will be administered in formulations suitable for injection in therapeutically effective amounts. Therapeutically effective amounts can range from 1 ng to 1,000 mg, from 1 μg to 500 mg, from 100 μg to 100 mg. Solubility co-solvents or detergents can be used to increase the storage stability. Additionally, or alternatively, mixed-phase or two-phase liquid systems can be used. Most preferably, chimeric molecule complexes will be formulated in a liquid carrier ready to use. However, it is contemplated that the chimeric molecule complexes can also be formulated in a dried form for reconstitution, by lyophilization or freeze drying.

EXAMPLES

The following examples provide exemplary guidance and are not intended to limit the scope of the inventive concept provided herein. Moreover, and unless otherwise indicated, all experiments were performed following standard protocols for cell culture and analysis well known in the art.

Lymphodepletion: Patients with a tumor are subjected to lymphodepletion using one or more pharmaceuticals (e.g., cyclophosphamide (cytoxan) and/or fludarabine (Fludara)) following protocols well known in the art.

Stimulation with ALT-803 or IL7/IL-15 TxM: Following lymphodepletion, patients are injected with ALT-803 or IL7/IL-15 TxM (typically subcutaneous) at dosages of about 10-50 mcg/kg. Stimulation can be performed between once daily and once weekly. Patients are then subjected to leukapheresis or blood draw and FACS isolation of TSCM cells. In most cases, the leukapheresis or blood draw and FACS isolation is performed 4-7 days after the stimulation.

Isolation of TSCM cells: Peripheral blood mononuclear cells (PBMCs) are harvested from patients having a tumor and PBMCs are isolated by Ficoll-Hypaque gradient separation (Lymphoprep, Fresenius). Enrichment can be done for CD3+ or CD8+ cells with Pan T Cell Isolation Kit II or CD8 Isolation Kit respectively (Miltenyi Biotech). Cells are labeled with anti-CD3, anti-CD45RA (BD Biosciences) and anti-CD62L (Exbio) fluorescent antibodies and FACS-purified into desired fractions $T_N$, $T_{CM}$, $T_{SCM}$, and $T_{EM}$ on a MoFlo MLS cell sorter (Dako). As desired, isolated T cells are further segregated into $T_{SCM}$ sub-population using $T_{SCM}$ specific markers (see FIG. 1).

In vitro cell culture: Isolated lymphocytes are cultured with: rhIL-2 at 300 IU/ml, rhIL-7 at 5 ng/ml (Peprotech) or rhIL-7, rhIL-15 at 5 ng/ml each (Peprotech), and IL-21 at 100 ng/ml. Cytokines and medium is replaced every 3-4 days. Alternatively, the cytokines are replaced by IL-7/IL-15/IL-21 TxM, typically at a concentration of between 15 and 200 ng/ml. Upon reaching a sufficient number of $T_{SCM}$ cells, growth medium is removed from the cells and replaced by ringer solution for infusion. Cells are promptly administered to the patient.

Figure 4:
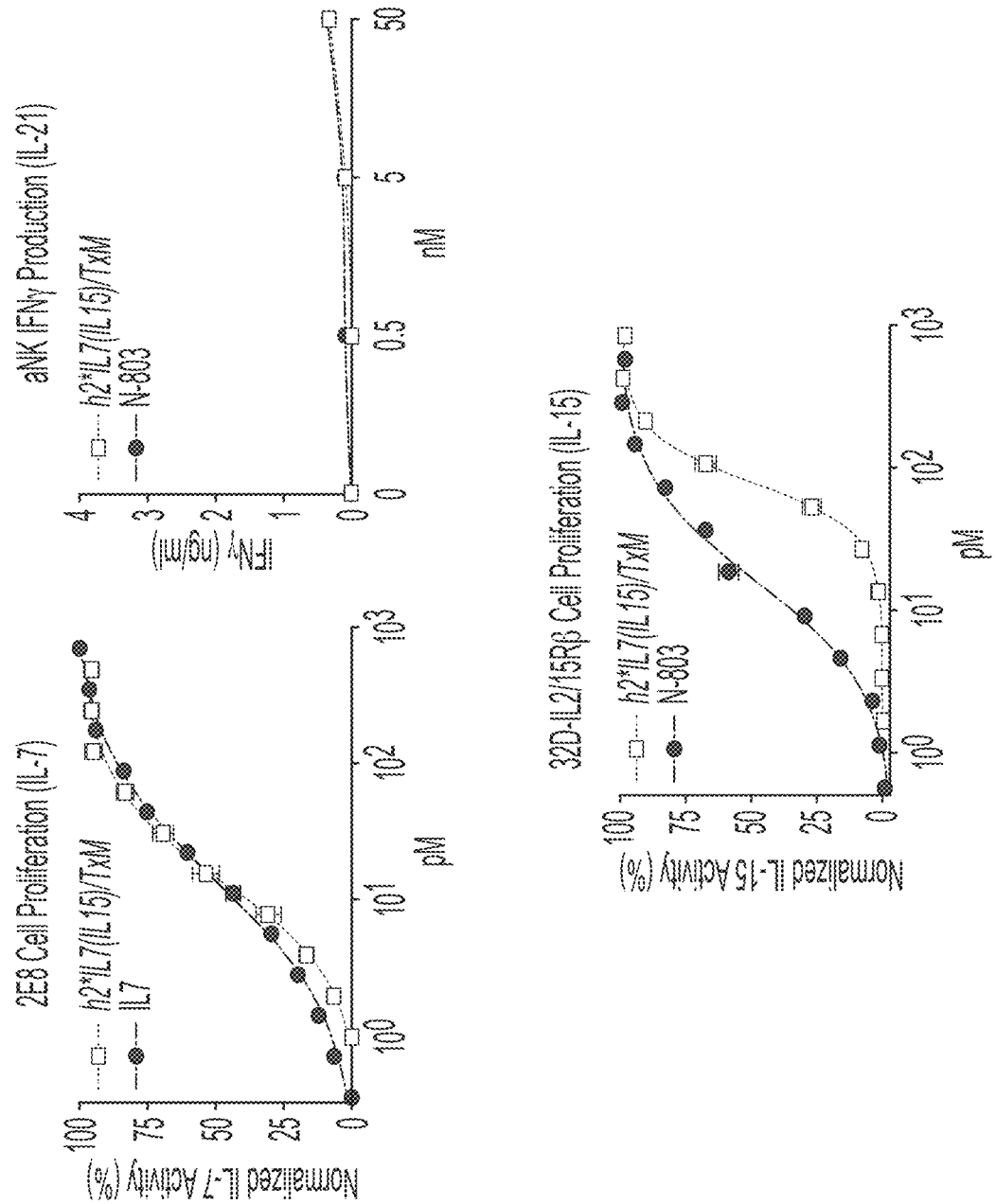
FIG. 4 shows exemplary results for cell proliferation and IFN-γ production using an exemplary chimeric molecule complex comprising an IL-7 portion and an IL-15 portion as compared to a chimeric molecule complex comprising an IL-15 portion (ALT-803 (N-803)).

FIG. 4 depicts exemplary results for activation of specific receptors of selected cells after activation with selected TxM constructs (IL15, IL7). More specifically, IL7 dependent 2E8 cells ($10^5$) were stimulated for 2 days with h2*IL7 (IL15)/TxM or IL7 and cell proliferation was assessed using PrestoBlue. The $EC_{50}$ of IL7 in h2*IL7 (IL15)/TxM is 13.3 pM. n=4 from 2 experiments. aNK cells ($2\times10^5$) were stimulated for 40 hours with h2*IL7 (IL15)/TxM or N-803 and production of IFNγ was measured by ELISA. n=2 from 1 experiment. IL2/15 dependent 32D-IL2/15Rβ cells ($10^4$) were stimulated for 3 days with h2*IL7 (IL15)/TxM or N-803 and cell proliferation was assessed using PrestoBlue. The $EC_{50}$ of IL15 in h2*IL7 (IL15)/TxM is 81.3 pM. n=4 from 2 experiments.

Figure 5:
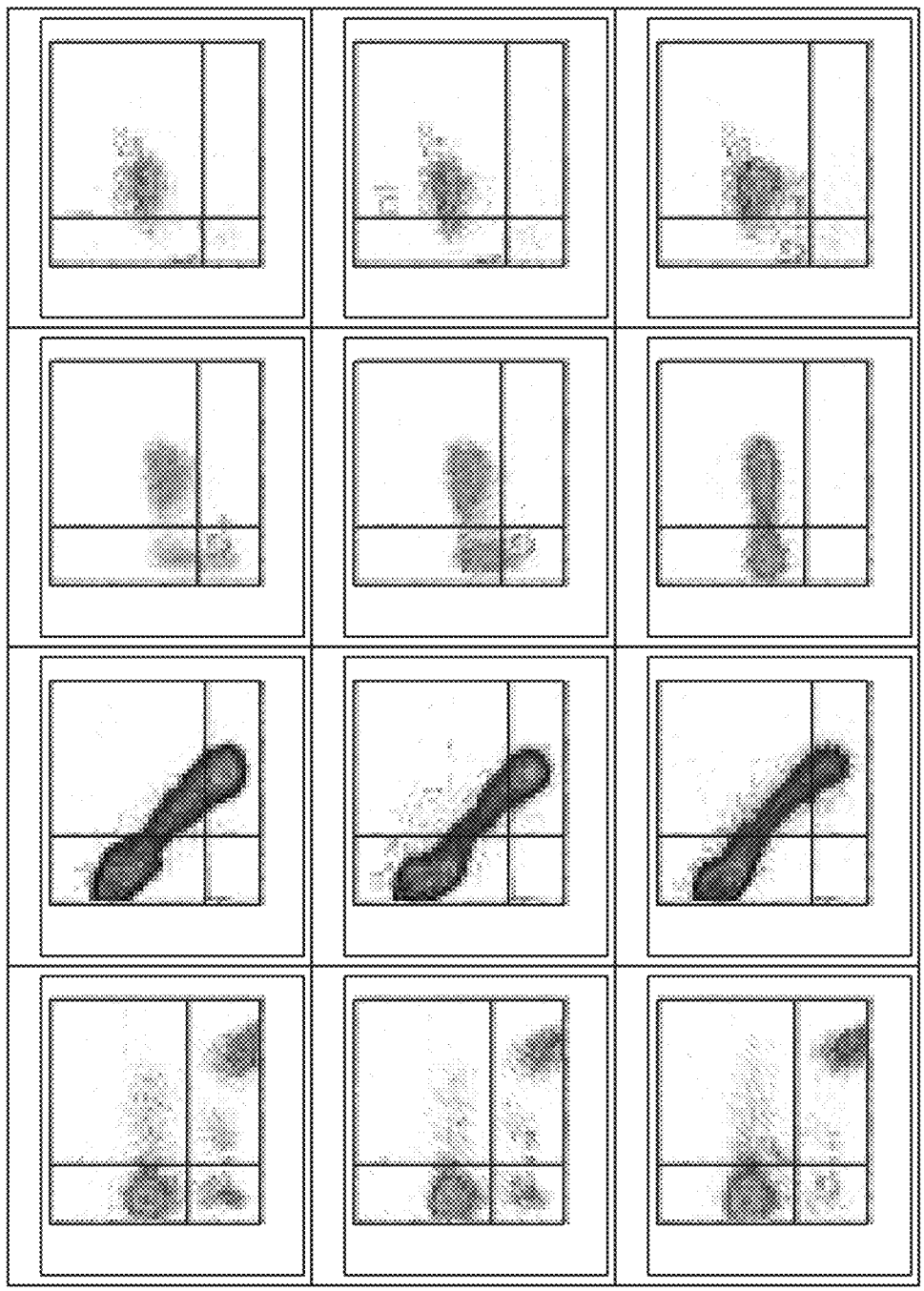
FIG. 5 depicts exemplary results for enrichment of $T_{SCM}$ cells after contact with an IL-7/21 TxM.
Figure 5:
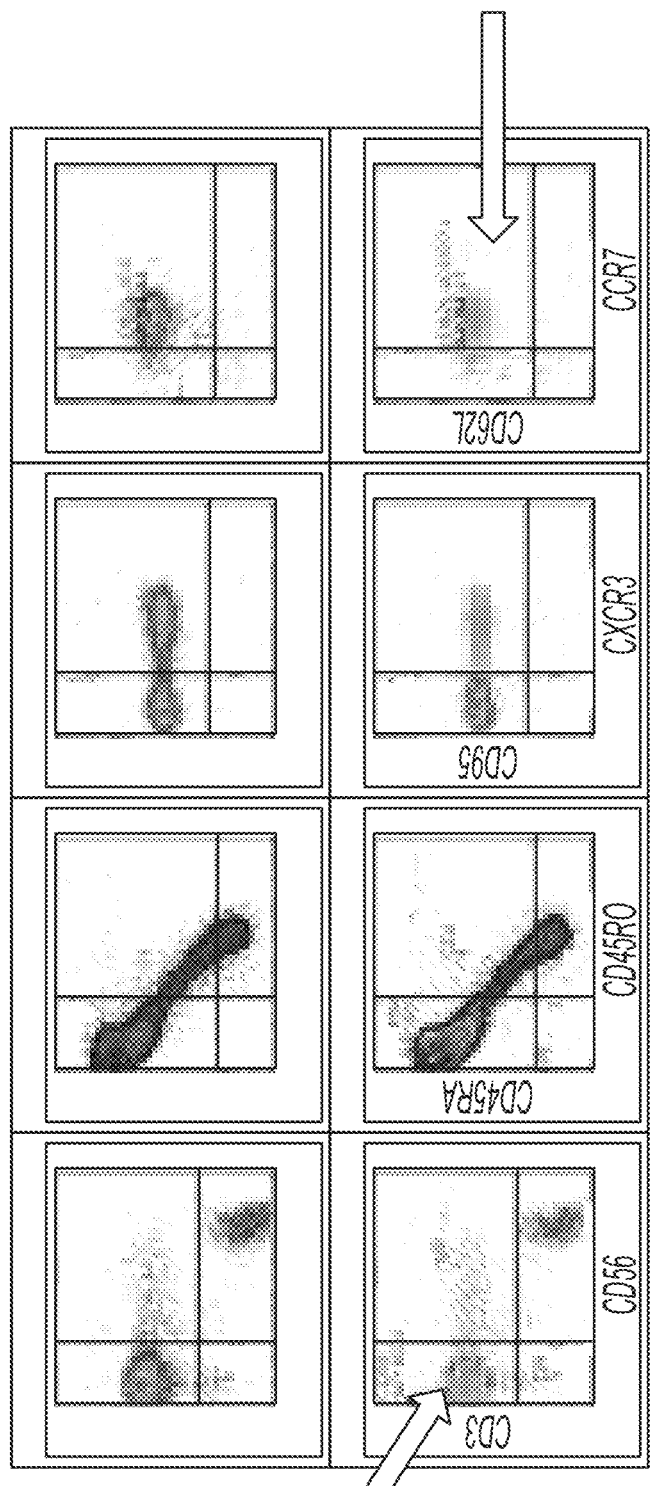

In yet further experiments, the inventors demonstrated that enrichment of stem cell-memory like T ($T_{SCM}$) cells could be facilitated by a IL-7/21 TxM. More specifically, peripheral blood mononuclear cells (PBMCs) were cultured in the presence of 0.8 nM N-803, 5 uM of the GSK-3 beta inhibitor TWS119, aCD3 (1 ng/mL), aCD28 (10 ng/ml), and increasing concentrations of IL-7/21 TxM from 0.1 nM to 10 nM. As can be seen from FIG. 5, the combination of IL-7/21 TxM and TWS119 yielded more CD3+ T cells, CD45RA+ and CD95+/CXCR3+ cells while maintaining the high percentage of CD62L and CCR7 double positive cells as in the presence of TWS119. It should be noted that all of these markers are characteristic of $T_{SCM}$s and IL-7/21 TxM appears to be further facilitating the $T_{SCM}$ enrichment in combination of TWS119.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Where the specification claims refers to at least one of something selected from the group consisting of A, B, C . . . and N, the text should be interpreted as requiring only one element from the group, not A plus N, or B plus N, etc.

What is claimed is:

1. A method of generating a therapeutic cell composition, the method comprising:
   administering to an individual a chimeric molecule complex comprising a first fusion protein comprising an IL15 portion and an IL7 portion; wherein the first fusion protein has the amino acid sequence of SEQ ID NO: 1, and a second fusion protein comprising an IL15RaSuFc portion and an IL21 portion, wherein the second fusion protein has the amino acid sequence of SEQ ID NO: 2, and wherein the IL15 portion of the first fusion protein is non-covalently bound to the IL15RaSuFc portion of the second fusion protein to thereby stimulate differentiation of naïve T ($T_N$) cells to stem cell memory T ($T_{SCM}$) cells;
   wherein the individual has a tumor with tumor cells that express a tumor associated antigen or a tumor and patient specific neoepitope;
   isolating the $T_{SCM}$ cells from the individual;
   in vitro expanding the isolated $T_{SCM}$ cells; and
   generating the therapeutic cell composition by formulating the expanded $T_{SCM}$ cells for injection into the individual.

2. The method of claim 1 further comprising a step of lymphodepletion before the step of administering the chimeric molecule complex, wherein lymphodepletion comprises administration to the patient of an effective amount of a chemotherapy or radiation.

3. The method of claim 1 wherein the $T_{SCM}$ cells are isolated from the individual using leukapheresis and FACS sorting, wherein the $T_{SCM}$ cells are sorted by expression of CD62L or CCR7.

4. The method of claim 1 further comprising a step of selecting from the isolated $T_{SCM}$ cells a population of cells that have a T cell receptor that binds the tumor associated antigen or the tumor and patient specific neoepitope.

5. The method of claim 1 wherein the step of in vitro expanding the isolated $T_{SCM}$ cells is performed using the chimeric molecule complex of claim 1.

6. The method of claim 1 wherein the step of in vitro expanding the isolated $T_{SCM}$ cells is performed in the presence of the tumor associated antigen or the tumor and patient specific neoepitope.

7. The method of claim 1 wherein the step of in vitro expanding the isolated $T_{SCM}$ cells is performed in the presence of dendritic cells of the individual.

* * * * *